United States Patent [19]

Takahashi et al.

[11] 4,071,413
[45] Jan. 31, 1978

[54] METHOD FOR DETERMINING FREE FATTY ACIDS IN BLOOD SERUM USING FATTY ACID ACTIVATING ENZYMES

[75] Inventors: Zyuro Takahashi, Itami; Chozo Hayashi, Nishinomiya, both of Japan

[73] Assignee: Ono Pharmaceutical Co., Ltd., Osaka, Japan

[21] Appl. No.: 681,941

[22] Filed: Apr. 30, 1976

[30] Foreign Application Priority Data

July 30, 1975 Japan .................................. 50-92134

[51] Int. Cl.² .......................................... G01N 31/14
[52] U.S. Cl. ............................................ 195/103.5 R
[58] Field of Search ................................ 195/103.5 R

[56] References Cited

U.S. PATENT DOCUMENTS 3,703,591 11/1972 Bucolo et al. ................. 195/103.5 R

OTHER PUBLICATIONS

Dixon et al., "Enzymes" 1964, AP Inc., Publishers N. Y., p. 577.
Bergmeyer, "Method of Enzymatic Analysis" 1974, Verlag Chemie Weinheim, AP Inc., N. Y. and London, pp. 2127–2129.
Bergmeyer, "Method of Enzymatic Analysis" 1974, Academic Press, Inc., New York, p. 310.

*Primary Examiner*—Alvin E. Tanenholtz
*Assistant Examiner*—C. A. Fan
*Attorney, Agent, or Firm*—Sughrue, Rothwell, Mion, Zinn and Macpeak

[57] ABSTRACT

A method for determining free fatty acids in blood serum by subjecting them to a series of enzymatic reactions in the same reaction system using an acyl coenzyme A-synthesizing enzyme, myokinase and pyruvate kinase, and measuring the resulting pyruvic acid.

12 Claims, No Drawings

METHOD FOR DETERMINING FREE FATTY ACIDS IN BLOOD SERUM USING FATTY ACID ACTIVATING ENZYMES

BACKGROUND OF THE INVENTION

1. Field of the Invention

This invention relates to a method for determining free fatty acids in blood serum, e.g., palmitic acid, myristic acid, rinoleic acid, rinolic acid, etc., using fatty acid activating enzymes. More specifically, it relates to a method for determining free fatty acids in blood serum using a series of enzymatic reactions in which an acyl coenzyme A synthesizing enzyme (acyl-Co A synthetase, E. C. 6.2.1.3) and two phosphate group converting enzymes, myokinase (E. C. 2.7.4.3) and pyruvate kinase (E. C. 2.7.1.40), are successively reacted to form pyruvic acid in proportion to the amount of the fatty acids.

2. Description of the Prior Art

The determination of free fatty acids in blood serum has heretofore been attempted by various methods, such as extracting the free fatty acids with a lipid solubilizing organic solvent, and neutralizing and titrating them with alkali, or converting the free fatty acids to copper salts by the action of copper nitrate and triethanolamine, extracting the copper salts with chloroform, and subjecting the extract to the action of a chelating agent such as diethyldithiocarbamate to permit coloration.

The former method, however, has the defect of unsatisfactory reproducibility due to various factors such as the complexity of operation ascribable to the use of organic solvents, the effects of the presence of organic acids, and technical errors ascribable to titration. The latter method also suffers from the defect that the operation is complicated because of the formation of copper salts and the use of organic solvents, and that there is an undesired or toxic effect of organic solvents particularly chloroform, on the human body which cannot be overlooked. Both of these methods are thus very difficult to standardize as clinical diagnostic tests because of the complexity of operation.

SUMMARY OF THE INVENTION

We performed various research in order to find a method for determining the amount of free fatty acids in blood serum which is free from the defects of the prior art. Our investigations led to the discovery that by subjecting the free fatty acids in blood serum to the action of an acyl-CoA synthetase in the presence of adenosine triphosphate (ATP) and coenzyme A (CoA), subjecting the resulting adenosine monophosphate (AMP) to the action of myokinase in the presence of ATP, and subjecting the resulting adenosine diphosphate (ADP) to the action of pyruvate kinase in the presence of phosphoenolpyruvic acid (PEP) in the same reaction system, each of the enzymatic reactions proceeds rapidly and quantitatively, and that the measurement of the resulting pyruvic acid can be performed easily by subjecting the resulting pyruvic acid to the action of lactate dehydrogenase (E.C. 1.1.1.27) in the presence of reduced nicotinamide adenine dinucleotide (NADH$_2$) and measuring the oxidation of NADH$_2$ by the decrease in optical density at 340 m$\mu$, or by subjecting it to the action of a hydrazine such as 2,4-dinitrophenyl hydrazine to form a hydrazone and measuring the increase in optical density at 450 m$\mu$ or 520 m$\mu$.

Accordingly, it is an object of this invention to provide an excellent method for determining the amount of free fatty acids in blood serum which uses a reduced amount of test specimen, comprises specific and simple reactions carried out in the same reaction system, and does not require the use of organic solvents.

Another object of this invention is to provide a novel method for determining the amount of free fatty acids in blood serum which can be standardized and is applicable to chemical analyses in clinical diagnosis.

The above objects can be achieved in accordance with this invention by a method for determining the amount of free fatty acids in blood serum using fatty acid activating enzymes, which comprises subjecting the free acids in blood serum to the action of an acyl CoA synthetase in the presence of adenosine triphosphate and coenzyme A, subjecting the resulting adenosine monophosphate to the action of myokinase in the presence of adenosine triphosphate, subjecting the resulting adenosine diphosphate to the action of pyruvate kinase in the presence of phosphoenolpyruvic acid, and measuring amount of the resulting pyruvic acid.

DETAILED DESCRIPTION OF THE INVENTION

To facilitate an understanding of the theory of the determination method of this invention, the series of enzymatic reactions of the present invention are schematically shown below.

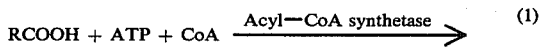
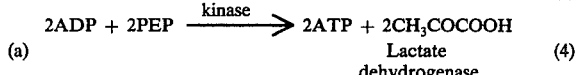

(a)

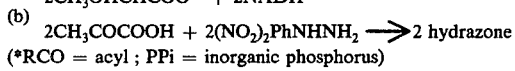

(b)

2CH$_3$COCOOH + 2(NO$_2$)$_2$PhNHNH$_2$ ⟶ 2 hydrazone (*RCO = acyl ; PPi = inorganic phosphorus)

The acyl-CoA synthetase, myokinase, pyruvate kinase and lactate hydrogenase used in the present invention have the enzyme numbers [6.2.1.3], [2.7.4.3], [2.7.1.40] and [1.1.1.27], respectively, according to the Report of the Enzyme Committee, International Union of Biochemistry. These enzymes may be of known sources, for example, the sources described for the corresponding enzymes numbers in "Enzyme Handbook" by Shiro Akabori (a Japanese language publication published by Asakura Shoten, Tokyo in 1966). For example, the acyl-CoA synthetase may be one prepared by partially purifying a liver microsome fraction of a rat caused to fast for 48 hours, on the basis of the Bar-Tana method [Bio. Chem. J., 122, 353 (1971)]. Many of the enzymes that can be used in the present invention are commercially available. Of course, the enzymes used in this invention are not limited to these known sources, but enzymes obtained by separation and purification from new sources can also be used.

The buffer used in the present invention can be any buffer which gives a pH range of about 6.9 to about 9.0, e.g., tris-hydrochloric acid buffer, phosphate buffer, borate buffer, Barbital sodium-hydrochloric buffer, etc., with tris-hydrochloric acid buffer being preferred.

In the performance of the invention, a buffer, buffer solutions of various enzymes (acyl-CoA-synthetase, myokinase, pyruvate kinase and lactate dehydrogenase), various substrates (fatty acids or serum specimens and CoA in reaction (1) above; AMP or ATP in reaction (2) above; PEP in reaction (3) above; and pyruvic acid in reaction (4) above) and buffer solutions of various coenzymes (ATP, AMP, ADP and $NADH_2$) are added to a serum specimen in proportions as set forth below, and enzymatic reactions are carried out.

| | |
|---|---|
| Acyl-CoA synthetase | 5-50 U/test |
| Myokinase | 0.2-1 U/test |
| Pyruvate kinase | 0.2-1 U/test |
| Lactate dehydrogenase | 10-30 U/test |
| ATP | 1-5 mg/test |
| CoA | 0.2-1 mg/test |
| PEP | 1-3 mg/test |
| $NADH_2$ | 2-10 mg/test |

Good results are obtained when a nonionic surface active agent such as polyoxyethylene ether (Triton X-100 (a registered trademark for a product of Rhom & Haas Co.)) is added to the enzymatic reaction solution in an amount of 0.01-1% by weight, preferably 0.05-3% by weight because such increases the affinity of the enzyme to the substrate(s). Polyoxyethylene sorbitan monooleate, polyoxyethylene sorbitan trioleate, polyoxyethylene sorbitan monostearate, etc., can also be used. Usually, such a surface active agent is added to the buffer in advance of the determination.

The series of enzymatic reactions involved, which proceeds sequentially but in the same reaction bath, are stopped when the free fatty acids have been consumed, but a suitable time of stopping the reactions can be selected by tracing the reactions according to the optical density to be measured. Usually, these reactions are carried out for about 5 to about 15 minutes. The reaction temperature is usually about 25° to about 40° C, and the reaction is usually carried out at a pH of about 6.9 to about 9.0. The pH of the reaction system is adjusted using tris-hydrochloric acid buffer prepared in accordance with the method of Gomori (Proc. Soc. Exptl. Biol. Med., 62 33 (1946)) and confirming by means of a pH meter. In the above enzymatic reactions, the chemical equilibrium of the acyl-CoA synthetase reaction is about 1. Typically the reactions are conducted at atmospheric pressure, but in theory nothing would prevent one performing the reactions at sub- or super-atmospheric pressure, though nothing would be gained thereby. However, favorable measurement results not attainable with a mere combination of known enzyme systems can be obtained since according to the method of this invention the AMP product in reaction (1) is at once converted to ADP in accordance with the reaction formula (2) and completely exhausted and the activation of the free fatty acids proceeds sufficiently because of the very small Km value (Michaelis constant) of this enzyme for the free fatty acids (non-esterified) G. M. Kellerman; J. Biol. Chem., 231 427 (1958)).

According to this invention, pyruvic acid is formed from a free fatty acid using an enzymatic system comprising the acyl-CoA synthetase, myokinase and pyruvate kinase wherein reactions are conducted sequentially in the manner described above. When the resulting pyruvic acid is measured by the enzymatic method comprising subjecting it to the action of lactate dehydrogenase in the presence of $NADH_2$ under the conditions set forth above and measuring a decrease in optical density of the $NADH_2$ oxidation, system at 340 mμ, the lactate dehydrogenase reaction can also be carried out in the same reaction system as the above series of enzymatic reactions. When it is measured by the hydrazone method comprising subjecting it to the action of a hydrazine such as 2,4-dinitrophenyl hydrazine to form a hydrazone and measuring the increase in optical density at 450 mμ or 520 mμ, the hydrazine is added to the reaction system to be reacted with the pyruvic acid produced after the termination of the series of enzymatic reactions (1) to (3).

From such a series of enzymatic reactions, it has been confirmed that the activity of 1 μ mole of free fatty acids corresponds to the change of 2 μ moles of $NADH_2$. Theoretically, it corresponds to 2 μ moles of pyruvic acid.

The following example is given to specifically illustrate the method of this invention, but is not intended in any way to limit the method of the invention.

EXAMPLE 1

A. Reagents

1. Buffer 100 mM tris-hydrochloric acid buffer (pH 8.0) containing 2 mg/ml of Triton X-100, 2 mM of EDTA 2Na and 50 mM of $MgCl_2$.

2. Enzyme-substrate solution

A solution prepared by dissolving 40 mg of ATP 2Na, 20 mg of PEP 2Na, 20 U of myokinase (Sigma Chemical Company, Grade III), 15 U of pyruvate kinase (Sigma Chemical Company, Type III) and 15 U of lactate dehydrogenase (Sigma Chemical Company, Type IV) in the buffer to a volume of 1 ml.

3. $NADH_2$ solution

A solution prepared by dissolving 4 mg of $NADH_2$ 2Na in the buffer to a volume of 1 ml.

4. CoA solution

A solution prepared by dissolving 12.5 mg of CoA in the buffer to a volume of 1 ml.

5. Acyl-CoA synthetase solution

A solution prepared by dissolving an enzyme obtained by separation and purification from a liver microsome of a rat in a buffer containing 20% glycerin and 1 mM dithiothreitol.

More particularly, the enzyme preparation was obtained according to the method of Bar-Tana (Biochem. J., 122 353 (1971)), i.e., by decapiting a rat fasted for 48 hours and weighing about 150 g, taking out the liver from the rat, perfusing the liver with a physiological salt solution until blood was completely removed therefrom, obtaining the microsome fraction from the liver in a conventional manner, desalting the fraction with butanol/acetone/ether, freezing drying the desalted fraction, which was then subjected to extraction and solubilization using sodium deoxycholate followed by subjecting the solubilized enzyme fraction of fractionation using ammonium sulfate twice to obtain a purified enzyme solution. By the above method a 700 U/ml sample of acyl-coA-synthetase was obtained. 50 μ-liters of this solution was used for the reaction.

B. Operation

To 1.0 ml of the buffer were added 50 μ-liters each of the NADH₂ solution, the enzyme-substrate solution, the test specimen (human blood serum) and the acyl-CoA synthetase solution (35 U), and preliminary reactions, i.e., blank reactions of the reactions (2), (3) and (4) above where the reaction conditions were the same as true reactions except that no CoA was added to the system (however, reaction (1) above and subsequent reactions (2), (3) and (4) above did proceed slightly due to the action of ATPase-like principle present in the blood serum to thereby increase in the OD value to some extent) were performed at 37° C until no increase of the OD value was observed i.e., reactions caused by impurities contained in the reagents used were completed. Apparent reactions, i.e., blank reactions of the myokinase reaction (2) and the subsequent reactions (3) and (4) were checked, and the optical density (O.D.) at the time when the apparent reactions were completed was recorded (O.D.; 0.14). Then, 20 μ-liters of the CoA solution was added, and a series of true enzymatic reactions (1) to (4) above were started. The reactions were observed by means of a recording instrument (an auto-recording spectrophotometer, Model 124, a product of Hitachi Limited), and the optical density (O.D.) at the end of the reactions (when the free fatty acid was consumed) recorded (O.D.; 0.34) and the absolute value of ΔO.D. calculated (O.D.; 0.34−0.14=0.20) by substracting the O.D. value at the starting point of the true enzymatic reactions from the O.D. value at the terminal point thereof where the free fatty acids in the test sample were exhausted completely and the reactions were stopped automatically, resulting in that the increase in the O.D. value was stopped. The absolute value of ΔO.D. corresponds to the amount of free fatty acids in the test blood serum sample.

A standard curve for free fatty acid was prepared by conducting reactions (1) to (4) above in the same manner except that various known amounts ranging from 0 to 1.0 mEq/l myristic acid ($C_{14}H_{28}O_2$, a product of Wako Jyunyaku Company) were used instead of blood serum, determining O.D. values corresponding to such amounts and plotting them. In the above procedure a clear straight line passing origin was obtained as a standard curve.

On the other hand, the amount of free fatty acid in blood serum was specimen from this standard curve (0.4 mEq/l in terms of myristic acid). Generally, the normal amount of free fatty acid level in human blood serum is 0.2–0.6 mEq/l in total.

EXAMPLE 2

A. Reagents

1. Buffer

Same as in Example 1.

2. Enzyme-substrate solution

Same as in Example 1 except that lactate dehydrogenase was absent.

3. CoA solution

Same as in Example 1.

4. Acyl CoA synthetase

Same as in Example 1.

5. 2,4-Dinitrophenylhydrazine solution

A solution prepared by dissolving 2 mg of 2,4-dinitrophenylhydrazine in 1 ml of 0.1 N HCl solution.

B. Operation

To 1.0 ml of the buffer were added 50 μ liters each of the enzyme-substrate solution, the test specimen (human blood serum) and the acyl CoA synthetase solution (35 U) and preliminary reactions were performed in the same manner as in Example 1 for 30 minutes. To the thus obtained solution was added 1 ml of the 2,4-dinitrophenylhydrazine solution (2 mg/ml 0.1N HCl) and the resultant solution was allowed to stand for 10 minutes at room temperature. To this solution 5 ml of 0.6N NaOH was added. The resultant solution was allowed to stand for 10 minutes at room temperature and the optical density at 520 ml recorded (O.D.; 0.07) in a similar manner as in Example 1 and a standard curve for free fatty acid was prepared by conducting reactions (1) to (4) above using known amounts (0–0.7 mEq/l) of the myristic acid identified above ($C_{14}H_{28}O_2$, a product of Wako Jyunyaku Company).

The amount of free fatty acids in the blood serum was determined from this standard curve (0.4 mEq/l in total, calculated as myristic acid).

While the invention has been described in detail and with reference to specific embodiments thereof, it will be apparent to one skilled in the art that various changes and modifications can be made therein without departing from the spirit and scope thereof.

What is claimed is:

1. A method for determining free fatty acids in blood serum, which comprises (A) preparing a standard curve for determining free fatty acids by subjecting known amounts of free fatty acid to (I) reaction with an acyl coenzyme A-synthesizing enzyme in the presence of adenosine triphosphate and coenzyme A, (2) subjecting the resulting adenosine monophosphate to reaction with myokinase in the presence of adenosine triphosphate, (3) subjecting the resulting adenosine diphosphate to reaction with pyruvate kinase in the presence of phosphoenolpyruvic acid, and (4) measuring the amount of the resulting pyruvic acid; (B) carrying out said reactions (1) through (4) in the blood serum in the absence of the coenzyme A in said reaction (I); (C) after step (B) carrying out said reactions (1) through (4) in the blood serum with the addition of coenzyme A in said reaction (I); and (D) determining amount of free fatty acids in said blood serum by subtracting the value determined in step (B) from the value determined in step (C) and comparing the result with the standard curve.

2. The method of claim 1 wherein the recited series of said enzymatic reactions are carried out at a temperature of about 25° to about 40° C and a pH of about 6.9 to about 9.0 for about 5 to about 15 minutes.

3. The method of claim 1 wherein the measurement of the amount of the pyruvic acid is carried out by subjecting the resulting pyruvic acid reaction with lactate dehydrogenase in the presence of reduced nitotinamide adenine dinucleotide and thereafter measuring the oxidation of the nitotinamide adenine dinucleotide by the decrease in optical density of the system at 340 mμ.

4. The method of claim 2 wherein the measurement of the amount of the pyruvic acid is carried out by subjecting the resulting pyruvic acid reaction with lactate dehydrogenase in the presence of reduced nitotinamide adenine dinucleotide and thereafter measuring the oxidation of the nitotinamide adenine dinucleotide by the decrease in optical density of the system at 340 mμ.

5. The method of claim 1 wherein the measurement of the pyruvic acid is carried out by reacting the resulting pyruvic acid with a hydrazine to form a hydrazone, and measuring the increase in optical density of the system at 450 mμ or 520 mμ.

6. The method of claim 2 wherein the measurement of the pyruvic acid is carried out by reacting the resulting pyruvic acid with a hydrazine to form a hydrazone, and measuring the increase in optical density of the system at 450 mμ or 520 mμ.

7. The method of claim 1 wherein the series of said enzymatic reactions are carried out in the presence of a nonionic surface active agent.

8. The method of claim 2 wherein the series of said enzymatic reactions are carried out in the presence of a nonionic surface active agent.

9. The method of claim 1, wherein the following components are utilized per determination of 50 ml of blood serum in the following proportions:
   The acyl coenzyme A-sensitizing enzyme in an amount of 5–50 U;
   the adenosine triphosphate in an amount of 1–5 mg;
   the coenzyme A in an amount of 0.2–1 mg;
   the myokinase in an amount of 0.2–1 U;
   the pyruvate kinase in an amount of 0.2–1 U;
   the phosphoenolpyruvic acid in an amount of 1–3 mg.

10. The method of claim 3 wherein said lactate dehydrogenase is used in an amount of 10–30 U/determination and said reduced nitotinamide adenine dinucleotide is used in an amount of 2–10 mg/determination.

11. The method of claim 2 wherein said lactate dehydrogenase is used in an amount of 10–30 U/determination and said reduced nitotinamide adenine dinucleotide is used in an amount of 2–10 mg/determination.

12. The method of claim 1 wherein said reactions are carried out sequentially in the same reaction bath.

* * * * *